United States Patent
Mitsuno et al.

(10) Patent No.: US 9,689,099 B2
(45) Date of Patent: Jun. 27, 2017

(54) PROCESS FOR PRODUCING STRETCH NONWOVEN FABRIC, AND STRETCH NONWOVEN FABRIC

(71) Applicant: UNICHARM CORPORATION, Shikokuchuo-shi, Ehime (JP)

(72) Inventors: Satoshi Mitsuno, Kanonji (JP); Jun Okuda, Kanonji (JP); Kou Detani, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 311 days.

(21) Appl. No.: 14/387,693

(22) PCT Filed: Dec. 19, 2012

(86) PCT No.: PCT/JP2012/082973
§ 371 (c)(1),
(2) Date: Sep. 24, 2014

(87) PCT Pub. No.: WO2013/145469
PCT Pub. Date: Oct. 3, 2013

(65) Prior Publication Data
US 2015/0322607 A1   Nov. 12, 2015

(30) Foreign Application Priority Data
Mar. 27, 2012 (JP) ................................. 2012-071572

(51) Int. Cl.
*D04H 13/00* (2006.01)
*D04H 3/007* (2012.01)
(Continued)

(52) U.S. Cl.
CPC ......... *D04H 13/00* (2013.01); *A61F 13/4902* (2013.01); *B32B 5/022* (2013.01);
(Continued)

(58) Field of Classification Search
CPC .......................... Y10T 428/24446; D04N 3/00
See application file for complete search history.

(56) References Cited

U.S. PATENT DOCUMENTS

2004/0222553 A1   11/2004   Desai et al.
2005/0142339 A1   6/2005   Price
(Continued)

FOREIGN PATENT DOCUMENTS

CN   101652508 A   2/2010
CN   101978106 A   2/2011
(Continued)

OTHER PUBLICATIONS

International Search Report in corresponding PCT Application No. PCT/JP2012/082973 dated Mar. 12, 2013, 2 pages.

*Primary Examiner* — William P Watkins, III
(74) *Attorney, Agent, or Firm* — Hauptman Ham, LLP

(57) ABSTRACT

The purpose of this disclosure is to provide a process for producing stretch nonwoven fabric having excellent stretchability. This production process has the following configuration. The process for producing stretch nonwoven fabric comprises: a step in which nonwoven fabric to be treated which comprises stretchable fibers and extensible fibers is unevenly stretched, while being conveyed, so that nonwoven fabric having both higher stretched regions and lower stretched regions is formed; and a step in which the nonwoven fabric having both higher stretched regions and lower stretched regions is heated for 0.1-10 seconds at a temperature which is 40° C. or higher but is lower than the melting point of the stretchable fibers. The production process is characterized in that in the nonwoven fabric having both higher stretched regions and lower stretched regions, the higher stretched regions and the lower stretched regions are parallel to the direction perpendicular to the conveying (Continued)

direction and are present alternately in the conveying direction.

18 Claims, 3 Drawing Sheets

(51) Int. Cl.
*D04H 1/4374* (2012.01)
*D06C 3/06* (2006.01)
*D04H 1/4291* (2012.01)
*D06C 7/00* (2006.01)
*A61F 13/49* (2006.01)
*D04H 3/02* (2006.01)
*B32B 5/02* (2006.01)
*B32B 5/26* (2006.01)
*B32B 7/02* (2006.01)

(52) U.S. Cl.
CPC ................. *B32B 5/26* (2013.01); *B32B 7/02* (2013.01); *D04H 1/4291* (2013.01); *D04H 1/4374* (2013.01); *D04H 3/007* (2013.01); *D04H 3/02* (2013.01); *D06C 3/06* (2013.01); *D06C 7/00* (2013.01); *B32B 2250/20* (2013.01); *B32B 2262/0253* (2013.01); *B32B 2274/00* (2013.01); *B32B 2307/51* (2013.01); *B32B 2307/728* (2013.01); *B32B 2307/73* (2013.01); *B32B 2432/00* (2013.01); *B32B 2555/00* (2013.01); *Y10T 428/24446* (2015.01); *Y10T 442/602* (2015.04)

(56) References Cited

U.S. PATENT DOCUMENTS

| | | |
|---|---|---|
| 2008/0166520 A1* | 7/2008 | Zafiroglu ............... B32B 7/08 428/136 |
| 2009/0035527 A1 | 2/2009 | Kobayashi et al. |
| 2010/0065984 A1 | 3/2010 | Akaki et al. |
| 2010/0209667 A1 | 8/2010 | Mitsuno et al. |
| 2011/0042849 A1 | 2/2011 | Akaki et al. |
| 2012/0164908 A1 | 6/2012 | Kunimoto |
| 2012/0181722 A1 | 7/2012 | Morita et al. |
| 2013/0031813 A1 | 2/2013 | Ishikawa et al. |
| 2013/0280481 A1 | 10/2013 | Mitsuno |

FOREIGN PATENT DOCUMENTS

| | | |
|---|---|---|
| EP | 2096201 A1 | 9/2009 |
| EP | 2221172 A1 | 8/2010 |
| JP | 2007-022066 A | 2/2007 |
| JP | 2007-321293 A | 12/2007 |
| JP | 2008-156785 A | 7/2008 |
| JP | 2011-080172 A | 4/2011 |
| JP | 2011-184833 A | 9/2011 |
| JP | 2012-077401 A | 4/2012 |
| WO | 2011/016343 A1 | 2/2011 |

* cited by examiner

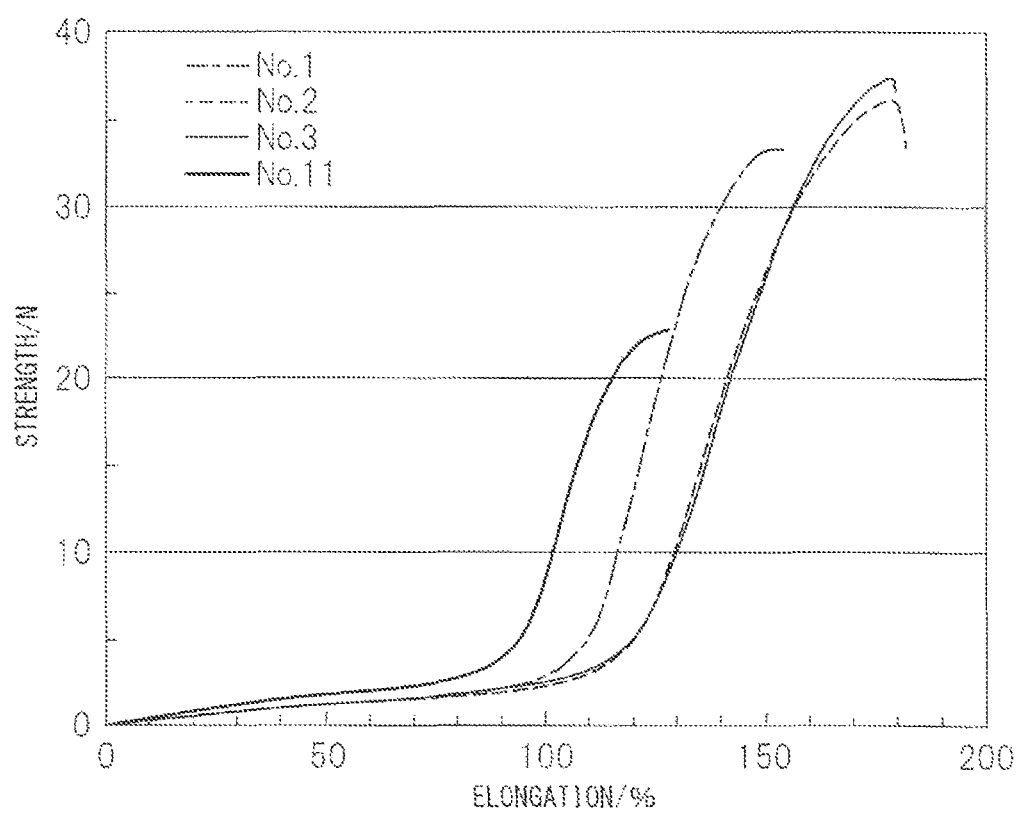

PROCESS FOR PRODUCING STRETCH NONWOVEN FABRIC, AND STRETCH NONWOVEN FABRIC

CROSS-REFERENCES TO RELATED APPLICATIONS

The present application is National Phase of International Application Number PCT/JP2012/082973 filed Dec. 19, 2012 and claims the priority of Japanese patent Application No. 2012-071572 filed Mar. 27, 2012.

TECHNICAL FIELD

The present disclosure relates to a method of producing a stretchable nonwoven fabric, and to a stretchable nonwoven fabric.

BACKGROUND ART

Nonwoven fabrics are used in a variety of different products, including absorbent articles such as sanitary products and disposable diapers, cleaning products such as wipers, and medical goods such as masks. The nonwoven fabrics used in such products usually have performance suited for the particular purposes of the products and their location of use.

With absorbent articles, for example, it is preferred for the nonwoven fabrics to be capable of expanding and contracting in response to bodily movement during wear or use, without creating an uncomfortable feeling for the user. With disposable diapers as well, it is preferred for the nonwoven fabrics to have high elasticity and strength sufficient to prevent tearing during extension, as well as satisfactory feel on the skin and air permeability.

The nonwoven fabrics having desired functions in such products are usually specially designed and produced for each product, and from the viewpoint of production cost and environmental protection, it is preferred for a nonwoven fabric having the desired performance to be one that can be easily produced by modification of a commercially available nonwoven fabric, for example.

In PTL 1, for example, where the aim is to provide a stretchable nonwoven fabric with further improved properties including stretchability, there is described a stretchable nonwoven fabric obtained by stretching a fiber sheet comprising an essentially nonelastic fiber layer made of continuous fibers formed by a spunbond method, on each side of an elastic fiber layer made of continuous fibers formed by a spunbond method, and then relaxing the tension to impart stretchability.

PTL 1 also states that the elastic fiber layer contains a thermoplastic elastomer.

CITATION LIST

Patent Literature

PTL 1 Japanese Unexamined Patent Publication No. 2007-321293

SUMMARY OF INVENTION

Technical Problem

In the stretchable nonwoven fabric described in PTL 1, however, the elastic fiber layer is a thermoplastic elastomer and therefore strain recovery after stretching and relaxation is delayed and the stretchability during use is often impaired. Particularly when the thermoplastic elastomer is a polyolefin-based elastomer, the strain recovery upon relaxation is delayed and the stretchability during use tends to be further impaired. Also, with the stretchable nonwoven fabric described in PTL 1, when the fiber sheet is stretched in the machine direction, tensile force continues to be applied to the fiber sheet in the machine direction even after stretching, and therefore relaxation is more difficult and stretchability during use is often impaired.

It is therefore an object of the present disclosure to provide a method of producing a stretchable nonwoven fabric with excellent stretchability.

Solution to Problems

The inventors of the present disclosure have found a method of producing a stretchable nonwoven fabric comprising the steps of non-homogeneous stretching of a nonwoven fabric to be treated comprising elastic fiber and extensible fiber while transporting the nonwoven fabric to be treated so that a nonwoven fabric with high-stretch regions and low-stretch regions is formed, and heating the nonwoven fabric with high-stretch regions and low-stretch regions for 0.1 to 10 seconds at a temperature of 40° C. or higher and below the melting point of the elastic fiber, wherein the nonwoven fabric having high-stretch regions and low-stretch regions has the high-stretch regions and low-stretch regions alternating in the machine direction, each parallel to the direction perpendicular to the machine direction.

Advantageous Effects of Invention

The method of producing a stretchable nonwoven fabric according to the present disclosure can produce a nonwoven fabric with excellent stretchability.

BRIEF DESCRIPTION OF DRAWINGS

FIG. 4 is a graph showing the results of a tensile test.

DESCRIPTION OF EMBODIMENTS

The method of the present disclosure will now be described in detail.

Figure 1:
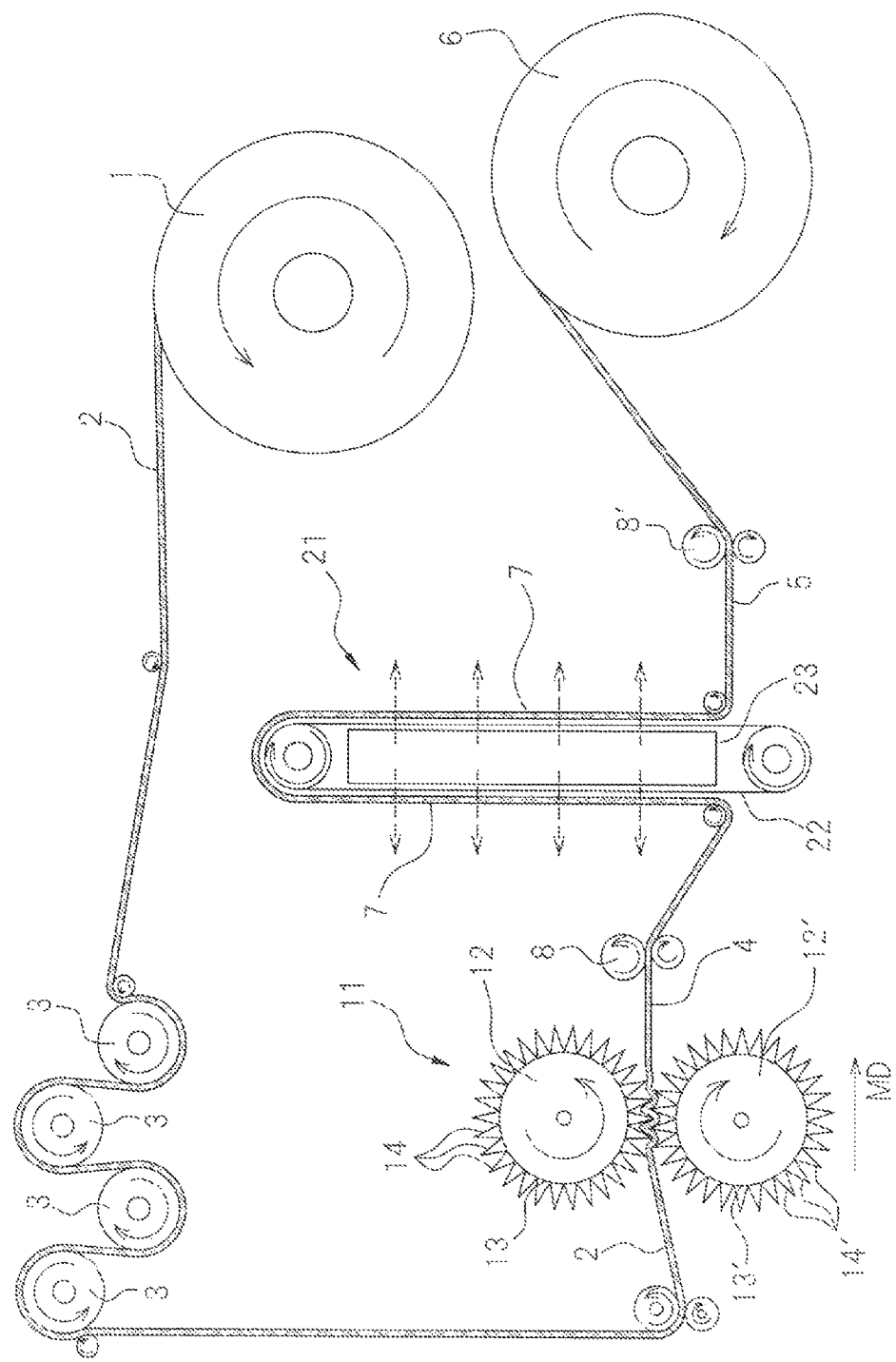
FIG. 1 is a diagram illustrating a method according to one embodiment of the present disclosure.

FIG. 1 is a diagram illustrating a method according to one embodiment of the present disclosure. In the embodiment illustrated in FIG. 1, a nonwoven fabric 2 to be treated that is fed out from a feed roll 1 is directed to preheating rolls 3, as a preheating treatment step. Next, as a non-homogeneous stretching step, the nonwoven fabric 2 to be treated that has passed through the preheating rolls 3 is subjected to gear stretching at a gear stretcher 11, to form a nonwoven fabric 4 having high-stretch regions and low-stretch regions. Next, the nonwoven fabric 4 with high-stretch regions and low-stretch regions is heated with a heating apparatus 21 as a heating step, to produce a stretchable nonwoven fabric 5. The produced stretchable nonwoven fabric 5 is then wound up with a take-up roll 6.

The method of the present disclosure comprises a step in which a nonwoven fabric to be treated comprising elastic fibers and extensible fibers is subjected to non-homogeneous stretching while being transported, so as to form a nonwoven fabric having high-stretch regions and low-stretch regions (this step will hereunder also be referred to as "non-homogeneous stretching step"). The nonwoven fabric having high-stretch regions and low-stretch regions has alternating high-stretch regions and low-stretch regions in the machine direction, which are each parallel to the direction perpendicular to the machine direction.

As used herein, "the nonwoven fabric having high-stretch regions and low-stretch regions has alternating high-stretch regions and low-stretch regions in the machine direction, which are each parallel to the direction perpendicular to the machine direction", may be more succinctly referred to as "the nonwoven fabric stretched in the machine direction and having high-stretch regions and low-stretch regions".

The nonwoven fabric to be treated is not particularly restricted so long as it comprises elastic fibers and extensible fibers, and for example, there may be mentioned (i) a nonwoven fabric comprising a layer that contains elastic fibers and extensible fibers, (ii) a nonwoven fabric comprising an elastic fiber layer and an extensible fiber layer, and (iii) a combination of the above.

Examples of nonwoven fabrics comprising layers that contain elastic fibers and extensible fibers include single-layer nonwoven fabrics, for example, single-layer nonwoven fabrics in which elastic fibers are mixed with extensible fibers, and single-layer nonwoven fabrics wherein elastic fibers and extensible fibers form composite fibers.

Examples of (ii) nonwoven fabrics comprising an elastic fiber layer and an extensible fiber layer include layered nonwoven fabrics with two, three or more layers, such as layered nonwoven fabrics with two layers comprising an elastic fiber layer and an extensible fiber layer, and layered nonwoven fabrics with three layers comprising two extensible fiber layers and an elastic fiber layer therebetween.

As used herein, "elastic fiber" means fiber that is capable of elastic elongation. More specifically, the elastic fiber is fiber that has a larger elastic limit than the maximum stress applied during formation and during expected use, and that is capable of elastic extension within the range of maximum stress during formation and during expected use. The maximum stress during formation and during expected use may be, for example, stress applied in the non-homogeneous stretching step, such as in the gear stretching.

The elastic fiber material is not particularly restricted so long as it is fiber with the stretchability specified above, and fibers made of a thermoplastic elastomer may be mentioned as an example.

Examples of thermoplastic elastomers include polyolefin-based elastomers, polyurethane-based elastomers, polystyrene-based elastomers, polyamide-based elastomers, polyester-based elastomers and their combinations. Polyolefin-based elastomers are preferred as thermoplastic elastomers, from the viewpoint of cost.

Polyolefin-based elastomers include amorphous or low crystalline ethylene/α-olefin copolymers, propylene/α-olefin random copolymers, propylene/ethylene/α-olefin random copolymers and the like, or their mixtures with crystalline polyolefins (for example, propylene homopolymers, copolymers of propylene and small amounts of α-olefins, high-density polyethylene, medium-density polyethylene, and the like).

Polyolefin-based elastomers are commercially available, and examples include TAFMER (α-olefin copolymer, trade name of Mitsui Chemicals, Inc.), Engage (ethylene-octene copolymer, trade name of Dupont Dow Elastomer) and Vistamaxx (polypropylene-based elastomer, trade name of ExxonMobil).

The polyolefin-based elastomer is preferably a polypropylene-based elastomer, and preferably a polypropylene-based elastomer (such as a propylene/α-olefin copolymer) having a propylene content of about 80 to about 90 mass % and a density of about 0.855 to about 0.880 g/cm$^3$.

Such a propylene/α-olefin copolymer having a low propylene content compared to conventional polypropylene-based elastomers and having a low density exhibit higher extension properties than conventional polypropylene-based elastomers.

The propylene/α-olefin copolymer has a melt flow rate (MFR) of preferably about 1 to about 1000 g/10 min, more preferably about 5 to about 500 g/10 min and even more preferably about 10 to about 100 g/10 min (ASTM D1238 230° C., 2160 g load), from the viewpoint of the spinning property, and especially resistance to yarn breakage during spinning.

Examples of α-olefins as polymerizing components in the propylene/α-olefin copolymer include approximately C2-C20 α-olefins, such as ethylene, 1-butene, 1-pentene, 3-methyl-1-butene, 1-hexene, 3-methyl-1-pentene, 4-methyl-1-pentene, 1-heptene, 1-octene, 1-nonene, 1-decene, 1-decene, 1-tetradecene, 1-hexadecene, 1-octadecene and 1-eicosene, as well as any desired combinations of the foregoing, with ethylene and 1-butene being preferred.

In one method according to an embodiment of the present disclosure, where the nonwoven fabric to be treated comprises an elastic fiber layer, the elastic fiber layer extends by 100% (twice the original length), and then after shrinkage, it has a residual strain, after extension, of preferably no greater than about 30% and more preferably no greater than about 20%. The elastic fiber layer preferably has this level of residual strain after extension, in either or both the machine direction and the direction perpendicular to the machine direction during production. As used herein, "the direction perpendicular to the machine direction" will sometimes be referred to as "the cross direction".

The elastic fiber is not particularly restricted in its fiber length, and for example, it may consist of staple fibers and continuous filaments, but preferably continuous filaments such as continuous filaments that are formed by a spunbond method. When the elastic fiber is continuous fiber, the resin extruded in a semi-molten state from the nozzle lip is continuously extended by cold air or mechanical draw, and therefore the fiber size is narrow and the fiber size variation is low. As a result, the texture is satisfactory as observed through the formed nonwoven fabric, and there is little variation in the extension properties of the nonwoven fabric.

From the viewpoint of air permeability and extension properties, the elastic fiber has a fiber size of preferably about 5 µm or greater and more preferably about 10 µm or greater, and it has a fiber size of preferably about 100 µm or smaller and more preferably about 40 µm or smaller.

As used herein, "extensible fiber" means fiber having a smaller elastic limit than the elastic limit of the aforementioned elastic fiber. More specifically, the extensible fiber is fiber having a smaller elastic limit than the maximum stress applied during formation, and capable of plastic deformation by the maximum stress applied during formation. The extensible fiber becomes thinner and longer by plastic deformation. Thus, the extensible fiber preferably has a fiber size selected in consideration of the fact that the fiber size narrows by the step described above.

As used herein, extensible fiber that has undergone plastic deformation by the stress of formation will sometimes be abbreviated as "elongated extensible fiber". An example of elongated extensible fiber is fiber having a uniform diameter, or fiber having a non-uniform diameter, such as one having partial thin sections (necking sections).

The maximum stress during formation may be, for example, stress applied in the non-homogeneous stretching step, such as in the gear stretching.

The extensible fiber is preferably fiber containing a polyolefin-based resin. For example, the extensible fiber may be (I) fiber formed from a polyolefin-based resin homopolymer or from a blend of different polyolefin-based resin homopolymers, or (II) composite fibers containing a polyolefin-based resin, core-sheath composite fibers having a polyolefin-based resin sheath, side-by-side composite fibers where one is a polyolefin, or split fibers where at least one split element is a polyolefin resin.

When the extensible fiber is a core-sheath composite fiber, it may be a core-sheath composite fiber in which the core is formed from PET or PP and the sheath is formed from low melting point PET, PP or PE. Because the core-sheath composite fiber has high heat sealability with elastic fibers, it may be suitably used when the nonwoven fabric to be treated has a layered structure with an elastic fiber layer and an extensible fiber layer, for example.

Examples of polyolefin-based resins include polyethylene, polypropylene and ethylene/α-olefin copolymer.

The extensible fibers are not particularly restricted in their fiber lengths, and there may be mentioned staple fibers and continuous filaments, for example. Similar to elastic fiber, the extensible fiber preferably consists of continuous filaments, such as continuous filaments formed by a spunbond method.

The extensible fiber has a fiber size of preferably about 1 to about 30 μm and more preferably about 10 to about 20 μm. The extensible fiber preferably has a smaller fiber size than the fiber size of the elastic fiber. This is because if the fiber size of the extensible fiber is small, the formed stretchable nonwoven fabric will have excellent flexibility, bulk and masking properties, as well as satisfactory feel on the skin.

The single-layer nonwoven fabric comprising a mixture of elastic fiber and extensible fiber may be a nonwoven fabric comprising elastic fiber and extensible fiber that is produced by any known method, such as an air-through nonwoven fabric, spunbond nonwoven fabric, point bond nonwoven fabric, spunlace nonwoven fabric, airlaid nonwoven fabric or meltblown nonwoven fabric, and from the viewpoint of strength of the obtained stretchable nonwoven fabric it is preferably a spunbond nonwoven fabric.

The single-layer nonwoven fabric formed of composite fibers comprising elastic fiber and extensible fiber may be, for example, a single-layer nonwoven fabric wherein the elastic fiber and extensible fiber form core-sheath fibers, for example core-sheath fiber wherein the elastic fiber is the core and the extensible fiber is the sheath, or core-sheath fiber wherein the extensible fiber is the core and the elastic fiber is the sheath, or side-by-side fibers, and for example, a nonwoven fabric produced by any known method, such as an air-through nonwoven fabric, spunbond nonwoven fabric, point bond nonwoven fabric, spunlace nonwoven fabric, airlaid nonwoven fabric or meltblown nonwoven fabric, and from the viewpoint of strength of the obtained stretchable nonwoven fabric it is preferably a spunbond nonwoven fabric.

According to an embodiment wherein the nonwoven fabric to be treated is a layered nonwoven fabric of two, three or more layers, there are no particular restrictions on the nonwoven fabric of each layer, similar to a single-layer nonwoven fabric, and for example, each may be a nonwoven fabric produced by any of various known methods, such as an air-through nonwoven fabric, spunbond nonwoven fabric, point bond nonwoven fabric, spunlace nonwoven fabric, airlaid nonwoven fabric or meltblown nonwoven fabric, while from the viewpoint of strength of the stretchable nonwoven fabric to be formed, it is preferably a spunbond nonwoven fabric.

According to an embodiment wherein the nonwoven fabric to be treated is a layered nonwoven fabric with two, three or more layers, the layering means for the layered nonwoven fabric is not particularly restricted, and for example, by bonding each nonwoven fabric with a hot-melt adhesive or the like it is possible to produce a layered nonwoven fabric as the nonwoven fabric to be treated, or by thermocompression bonding of the layered nonwoven fabrics with an embossing roll or the like, it is possible to produce a layered nonwoven fabric as the nonwoven fabric to be treated.

The pattern of the embossing roll to be used for the thermocompression bonding may be, for example, a circular, rhomboid or elliptical pattern. From the viewpoint of feel on the skin and stretchability, the area ratio of the thermocompression bonded sections is preferably about 1% to about 30%, more preferably about 2% to about 25% and even more preferably about 3% to about 20%. The area ratio of the thermocompression bonded sections is the total area of the thermocompression bonded sections divided by the area of the nonwoven fabric to be treated, multiplied by 100.

In the embossing roll to be used for the thermocompression bonding, the temperature of the upper and lower rolls may be the same or different. The temperature of the upper and lower rolls is preferably a lower temperature than the lower melting point of the extensible fiber or elastic fiber, so that the fibers do not fuse onto the rolls. For example, if the extensible fiber is fiber composed of polypropylene, the temperature of the upper and lower rolls is preferably about 100° C. to about 160° C. The thermocompression bonding pressure is preferably about 100 to about 1000 N/cm, for uniform thermocompression bonding of the fibers in the embossed sections.

In a method according to an embodiment in which the nonwoven fabric to be treated has a layered structure comprising an elastic fiber layer and an extensible fiber layer, and especially an embodiment of the present disclosure in which the nonwoven fabric to be treated has a three-layer structure comprising two extensible fiber layers and an elastic fiber layer therebetween, the extensible fiber layer has a basis weight of preferably about 1 to about 60 g/m² and more preferably about 3 to about 15 g/m². If the basis weight is less than about 1 g/m² it is difficult to uniformly cover the surface of the elastic fiber layer, and if the basis weight is greater than about 60 g/m², the residual strain after non-homogeneous stretching will tend to be increased.

In a method according to an embodiment in which the nonwoven fabric to be treated has a layered structure comprising an elastic fiber layer and an extensible fiber layer, and especially an embodiment of the present disclosure in which the nonwoven fabric to be treated has a three-layer structure comprising two extensible fiber layers and an elastic fiber layer therebetween, the elastic fiber layer has a basis weight larger than the basis weight of the extensible fiber layer, specifically a basis weight of preferably about 3 to about 80 g/m² and more preferably about 5 to about 40 g/m², from the viewpoint of stretchability and residual strain after non-homogeneous stretching.

As used herein, the residual strain after non-homogeneous stretching is the value determined by the following formula:

Residual strain after non-homogeneous stretching $(\%)=100\times(L_1-L_0)/L_0$ where the prescribed length $L_0$ of the nonwoven fabric to be treated (in the machine direction, during transport under tensile force) is converted to the length $L_1$ (machine direction, during transport) after non-homogeneous stretching, i.e. in the nonwoven fabric having high-stretch regions and low-stretch regions.

In the method according to one embodiment of the present disclosure, in the non-homogeneous stretching step, the nonwoven fabric to be treated is subjected to non-homogeneous stretching to have a residual strain after non-homogeneous stretching of generally about 3% to about 50%, more generally about 4% to about 45% and even more generally about 5% to about 40%. Also, in the method according to one embodiment of the present disclosure, in the non-homogeneous stretching step, the nonwoven fabric to be treated is selected as a nonwoven fabric to be treated having a residual strain after non-homogeneous stretching of generally about 3% to about 50%, more generally about 4% to about 45% and even more generally about 5% to about 40%.

In a method according to a different embodiment of the present disclosure, in which the nonwoven fabric to be treated has a layered structure comprising an elastic fiber layer and an extensible fiber layer, and especially an embodiment of the present disclosure in which the nonwoven fabric to be treated has a three-layer structure comprising two extensible fiber layers and an elastic fiber layer therebetween, from the viewpoint of cost the elastic fiber layer has a smaller basis weight than the basis weight of the extensible fiber layer.

As mentioned above, there are no particular restrictions on the fiber lengths of the elastic fiber and extensible fiber, and for example, they may be staple fibers or continuous filaments. When the nonwoven fabric to be treated includes two or more fibers such as the extensible fiber and elastic fiber, the fiber lengths of the fibers may be the same or different.

In a method according to one embodiment of the present disclosure, the nonwoven fabric to be treated is hydrophilic. If the nonwoven fabric to be treated is hydrophilic, the stretchable nonwoven fabric that is produced will tend to be hydrophilic, and when it is contacted with hydrophilic excreta (urine, sweat, feces and the like) when used in a disposable diaper, the excreta do not stop at the surface of the nonwoven fabric but easily pass through to the interior of the nonwoven fabric.

Examples for the nonwoven fabric to be treated having a hydrophilic property include nonwoven fabrics produced by treatment of a hydrophobic nonwoven fabric with a hydrophilic agent, nonwoven fabrics produced from composite fibers incorporating a hydrophilic agent, and nonwoven fabrics coated with a surfactant.

The non-homogeneous stretching step is carried out in the nonwoven fabric to be treated partially (i) to destroy the points of fiber contact in the nonwoven fabric and create a partial web state of the anchored fibers, and/or (ii) to form elongated extensible fiber between the points of fiber contact in the nonwoven fabric.

Because the elongated extensible fiber has the fibers oriented in the thickness direction after the heating step described below, the bulk is high and the cushioning properties of the produced stretchable nonwoven fabric can be increased. Also, because the elongated extensible fiber has a small fiber size, the feel on the skin of the produced stretchable nonwoven fabric can be improved. In addition, since a certain degree of extension of the elongated extensible fiber can increase the fiber strength and improve the strength of the nonwoven fabric, the stretchable nonwoven fabric produced can be resistant to expansion within a given range, without being excessively expanded.

Since the elastic fiber has a higher elastic limit than the stress applied during the non-homogeneous stretching step, the elastic fiber that has been temporarily extended during the non-homogeneous stretching step can undergo heat shrinkage in the subsequent heating step.

The joining points may be heat sealing points, when the nonwoven fabric to be treated is an air-through nonwoven fabric, or they may be thermocompression bonding points when the nonwoven fabric to be treated is a spunbond nonwoven fabric or point bond nonwoven fabric, and they may be fiber tangling points when the nonwoven fabric to be treated is a spunlace nonwoven fabric.

As used herein, "high-stretch region" means a region that has been stretched so that the degree of extension of the elongated extensible fiber is higher than in the low-stretch regions, while "low-stretch region" means a region that has been stretched so that the degree of extension of the elongated extensible fiber is lower than in the high-stretch regions, and it includes regions in which no elongated extensible fiber has been formed, i.e. unstretched regions.

Also as used herein, the term "non-homogeneous stretching" refers to stretching so as to form a nonwoven fabric having high-stretch regions and low-stretch regions, or in other words, stretching so as to form a nonwoven fabric having different degrees of extension of the elongated extensible fiber, depending on the location.

The non-homogeneous stretching step is not particularly restricted so long as it is means allowing formation of a nonwoven fabric stretched in the machine direction and having high-stretch regions and low-stretch regions, and it may be carried out by any desired means, such as passing the nonwoven fabric to be treated through the gap between a pair of gear rolls each having a rotational axis line perpendicular to the machine direction and rotating while engaging the plurality of teeth situated around the outer peripheral surface of the pair of gear rolls and parallel to the rotational axis line (this will also be referred to as "gear stretching" throughout the present specification).

The gear stretcher 11 shown in FIG. 1 has a pair of gear rolls 12 and 12'. A plurality of teeth 14 and 14' are situated around the outer peripheral surfaces 13 and 13' of the gear rolls 12 and 12'. In the gear stretcher 11 shown in FIG. 1, the rotational axis lines of the gear rolls 12 and 12' are both perpendicular to the machine direction of the nonwoven fabric. The plurality of teeth 14 and 14' are situated on the outer peripheral surfaces 13 and 13' in a manner parallel to the rotational axis lines.

In the gear stretcher 11 shown in FIG. 1, the nonwoven fabric to be treated 2 is passed through the gap between the gear rolls of the pair of gear rolls 12 and 12', and when it passes through the gear rolls 12 and 12', the nonwoven fabric to be treated 2 is stretched by the mutually engaging plurality of teeth 14 and 14' of the gear rolls 12 and 12', on the three-point bending principle, to form a nonwoven fabric 4 having high-stretch regions and low-stretch regions. The nonwoven fabric 4 having high-stretch regions and low-stretch regions has alternating high-stretch regions and low-stretch regions in the machine direction, which are parallel to the cross direction.

In the nonwoven fabric to be treated 2, the nonwoven fabric is anchored in the regions that are in contact with the tips of the plurality of teeth 14 and 14', and therefore undergoes little or no stretching, forming the low-stretch regions. On the other hand, in the regions of the nonwoven fabric to be treated 2 that do not contact the tips of the plurality of teeth 14 and 14', i.e. the regions between the tips of the teeth 14 and the tips of the teeth 14', the nonwoven fabric is widely stretched to form high-stretch regions.

In such a gear stretcher 11, the gear pitch is preferably about 1 to about 10 mm and more preferably about 2 to about 6 mm. If the gear pitch is less than about 1 mm it will be necessary to narrow the gear blades, often resulting in partial tearing of the nonwoven fabric to be treated 2. If the gear pitch P is greater than about 10 mm the draw ratio will be low and it may be difficult to form elongated extensible fiber.

Figure 2:
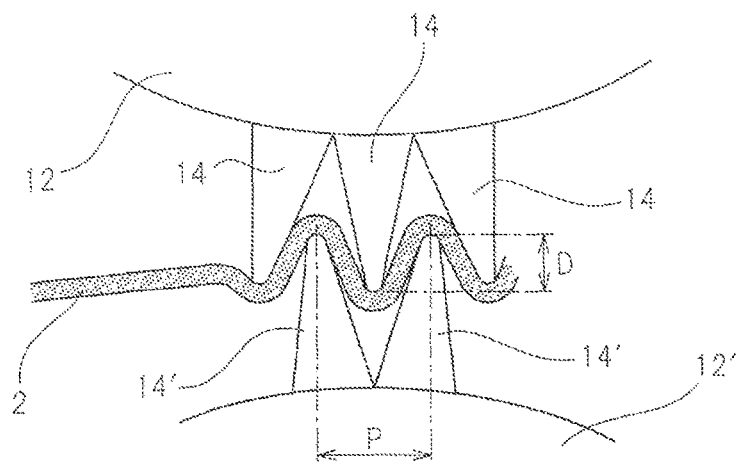
FIG. 2 is a magnified view of the area near the gear roll gap between the pair of gear rolls 12 and 12' of the gear stretcher 11 shown in FIG. 1.

FIG. 2 is a magnified view of the gear roll gap between the pair of gear rolls 12 and 12' of the gear stretcher 11 shown in FIG. 1. The gear pitch is the spacing between one tooth and another tooth of the same gear roll, as denoted by the symbol P in FIG. 2.

In this gear stretcher 11, the gear tooth cutting depth is preferably about 0.5 mm or greater. If the gear tooth cutting depth is less than about 0.5 mm, stretching of the nonwoven fabric to be treated 2 may be inadequate and it may be difficult to form high-stretch regions.

The gear tooth cutting depth is the depth at the section where a tooth 14 of the top gear roll 12 and a tooth 14' of the bottom gear roll 12' overlap, as denoted by the symbol D in FIG. 2.

For a nonwoven fabric stretched in the machine direction and having high-stretch regions and low-stretch regions, the draw ratio for each gear stretching is preferably about 30-400% and more preferably about 50-200%. If the draw ratio is lower than about 30% the elongated extensible fiber may not be formed, and if the draw ratio is higher than about 400%, the strength of the nonwoven fabric stretched in the machine direction and having high-stretch regions and low-stretch regions will tend to be weakened and the elongated extensible fiber will tend to be shed preferentially, often causing transport problems, and/or the extensible fiber may undergo breakage.

As used herein, the term "draw ratio" refers to the value calculated by the following formula:

$$\text{Draw ratio } (\%) = 100 \times \left[ \frac{\sqrt{P^2 + 4D^2}}{P} - 1 \right] \quad \text{[Formula 1]}$$

wherein P is the gear pitch and D is the gear tooth cutting depth.

In the embodiment shown in FIG. 1, the nonwoven fabric to be treated 2 passes through a plurality of preheating rolls 3 which are being transported, as a preheating treatment step before the non-homogeneous stretching step. The preheating treatment step is carried out in order to further facilitate extension of the extensible fiber, and preferably it is carried out by passing the nonwoven fabric to be treated 2 between one or a pair of rolls that have been heated to a temperature of about 30° C. or higher and no higher than the melting point of the elastic fiber, and more preferably to a temperature of about 40° C. to about 100° C.

The embodiment shown in FIG. 1 includes a preheating treatment step, but in the method of the present disclosure the preheating treatment step is an optional step, and a method according to another embodiment of the present disclosure does not include a preheating treatment step.

The method of the present disclosure includes a step of heating the nonwoven fabric having high-stretch regions and low-stretch regions, at a temperature of 40° C. or higher and below the melting point of the elastic fiber, for 0.1 to 10 seconds (this step will also be referred to simply as "heating step").

As used herein, the term "melting point" refers to the peak top temperature for the endothermic peak during conversion from solid to liquid, upon measurement with a differential scanning calorimetry analyzer at a temperature-elevating rate of 10° C./min.

In the embodiment shown in FIG. 1, the nonwoven fabric 4 having high-stretch regions and low-stretch regions, formed by the non-homogeneous stretching step, must be continuously transported while under application of a fixed tensile force, in order to stabilize the dimensions of the nonwoven fabric thereafter. However, because the nonwoven fabric 4 having high-stretch regions and low-stretch regions has reduced strength of the nonwoven fabric itself due to the non-homogeneous stretching step, the extended state is continuously held under the tensile force with virtually no shrinkage.

As a result, the nonwoven fabric is anchored in an extended state and cannot easily return to the original dimensions. Particularly when the elastic fiber is fiber composed of a polyolefin-based elastomer, the soft segment portions that exhibit stretchability are formed of an olefin, and therefore when the extended state is held, the molecular chains undergo partial crystallization in that state and the residual strain after non-homogeneous stretching is increased, while it becomes difficult to restore the original state.

Thus, by adding heat to the soft segment sections that are held in an extended state and have undergone partial crystallization, presumably molecular motion increases and it is possible to accomplish heat shrinkage of the elastic fibers.

In the embodiment shown in FIG. 1, the heating step is carried out following the non-homogeneous stretching step, but in a method according to another embodiment of the present disclosure, this includes a process in which the nonwoven fabric having high-stretch regions and low-stretch regions that has been formed by the non-homogeneous stretching step is first taken up by the take-up roll and then the nonwoven fabric having high-stretch regions and low-stretch regions is wound out from the take-up roll and subjected to a heating step. However, this embodiment also entails the problem that the original state is difficult to restore.

The heating step is not particularly restricted so long as it can accomplish heating of the nonwoven fabric having high-stretch regions and low-stretch regions at a temperature of 40° C. or higher and below the melting point of the elastic fiber, for between about 0.1 and about 10 seconds, and for example, it may involve (a) direct heating of the nonwoven fabric with high-stretch regions and low-stretch regions using a heated roll, (b) contacting a heated fluid (for example, heated air or steam) with a nonwoven fabric having high-stretch regions and low-stretch regions, or (c) irradiating a nonwoven fabric having high-stretch regions and low-stretch regions with infrared rays, high frequency rays or the like. Processes (a) to (c) above may be carried out while transporting the nonwoven fabric having high-stretch regions and low-stretch regions.

Among processes (a) to (c), from the viewpoint of allowing uniform heating of the entire nonwoven fabric having high-stretch regions and low-stretch regions, there is preferred (b) contacting a heated fluid (for example, heated air or steam) with a nonwoven fabric having high-stretch regions and low-stretch regions.

The means for contacting a heated fluid (for example, heated air or steam) with a nonwoven fabric having high-stretch regions and low-stretch regions is not particularly restricted, and for example, a known air-through method may be employed. The aforementioned air-through method is a method in which a sample is placed on a support such as a moving conveyor and heated fluid is discharged from the sample side or the support side, and then the heated fluid is contacted with the sample and, for example, the heated fluid is passed through the sample interior.

The moving conveyor may be a known plastic net, wire mesh, metal punching plate, screen mesh or the like, but considering that the nonwoven fabric having high-stretch regions and low-stretch regions undergoes heat shrinkage by the heating step and that the length in the machine direction may vary with time, it is preferably one with low friction with the nonwoven fabric to be heated and with high slidability, and for example, a metal punching plate or screen mesh may be mentioned.

The heating apparatus 21 shown in FIG. 1 has a moving conveyor 22 and a heated fluid discharge device 23, and the heated fluid (indicated by dotted line arrows) passes through from the moving conveyor 22 side to the interior of the nonwoven fabric 7 to be heated, and is discharged to the outside.

As used herein, "nonwoven fabric to be heated in the heating step" may be referred to simply as "nonwoven fabric to be heated".

In FIG. 1, as heat proceeds from the heating apparatus 21, the nonwoven fabric to be heated 7 undergoes heat shrinkage in the machine direction. Thus, when tensile force is applied in the machine direction of the nonwoven fabric to be heated, for example when the nonwoven fabric to be heated is continuous, such as when the nonwoven fabric to be treated wrapped around the wind-out roll is continuously treated and taken up with a take-up roll, the transport speed of the nonwoven fabric is preferably varied before and after the heating apparatus 21. Specifically, in FIG. 1, the transport speed of the stretchable nonwoven fabric 5 after the heating apparatus 21 (the transport speed by the transport roller 8') is preferably slower than the transport speed of the nonwoven fabric having high-stretch regions and low-stretch regions 4 before the heating apparatus 21 (the transport speed by the transport roller 8).

The transport speed varies according to the degree of heat shrinkage of the nonwoven fabric to be heated, and for example, the transport speed of the stretchable nonwoven fabric is preferably slower than the transport speed of the nonwoven fabric having high-stretch regions and low-stretch regions, and the transport speed of the stretchable nonwoven fabric is preferably a speed of about 0.30 to about 0.99 times, more preferably about 0.40 to about 0.95 times and even more preferably about 0.50 to about 0.92 times the transport speed of the nonwoven fabric having high-stretch regions and low-stretch regions.

In the heating step, on the other hand, when tensile force is not being applied to the nonwoven fabric to be heated in the machine direction, for example, when the nonwoven fabric having high-stretch regions and low-stretch regions is split into several parts and placed on the support without tensile force being applied in the machine direction, it is possible to freely accomplish heat shrinkage of the nonwoven fabric to be heated, and therefore the transport speed of the stretchable nonwoven fabric and the transport speed of the nonwoven fabric having high-stretch regions and low-stretch regions may be either the same or different.

Since it is possible to freely accomplish heat shrinkage of the nonwoven fabric to be heated in an embodiment such as shown in FIG. 1 where a heated fluid passes through the interior of the nonwoven fabric to be heated, the heated fluid preferably has a flow rate of about 0.1 to about 3.0 m/s. If the flow rate is less than about 0.1 m/s, temperature variation may occur in the cross direction of the nonwoven fabric to be heated, producing a difference in heat shrinkage factor of the nonwoven fabric. If the flow rate exceeds about 3.0 m/s, the nonwoven fabric to be heated may become anchored, inhibiting heat shrinkage.

In the heating step, the nonwoven fabric having high-stretch regions and low-stretch regions is heated at a temperature of about 40° C. or higher and below the melting point of the elastic fiber, and for example, it is heated at about 40° C. to about 160° C., preferably about 50° C. to about 150° C. and even more preferably about 60° C. to about 140° C. If the temperature is lower than about 40° C. the elastic fiber will tend to be resistant to heat shrinkage, and if the temperature is at or above the melting point of the elastic fiber, the elastic fiber may melt and fuse with the other fibers.

In most cases with elastic fiber and extensible fiber, the elastic fiber has a lower heat of fusion and therefore the elastic fiber can undergo shrinkage more rapidly than the initial melting of the extensible fiber.

In the heating step, the nonwoven fabric having high-stretch regions and low-stretch regions is heated for between about 0.1 and about 10 seconds, preferably about 0.5 to 8 seconds and more preferably about 1 to 6 seconds. If this time is shorter than about 0.1 second the elastic fiber may be resistant to heat shrinkage, and variation may occur in the heat shrinkage of the elastic fiber. If the time exceeds about 10 seconds, the elastic fiber may melt and fuse with the other fibers.

In the heating step, the nonwoven fabric having high-stretch regions and low-stretch regions is heated to a heat shrinkage in the range of preferably about 30% to about 99%, more preferably about 40% to about 95% and even more preferably about 50% to about 92% in the machine direction. If the nonwoven fabric having high-stretch regions and low-stretch regions undergoes heat shrinkage of less than about 30%, heat shrinkage may proceed too far to an inferior degree of stretchability, tending to produce hardness. If the nonwoven fabric having high-stretch regions and low-stretch regions undergoes heat shrinkage exceeding about 99%, the heat shrinkage will be insufficient and the stretchability will tend to be inferior.

Stated differently, in the heating step, the nonwoven fabric having high-stretch regions and low-stretch regions has a heat shrinkage factor of preferably about 30% to about 99%, more preferably about 40% to about 95% and even more preferably about 50% to about 92%.

As used herein, "heat shrinkage factor" means the value determined by the following formula:

$$\text{Heat shrinkage factor (\%)} = 100 \times L_2/L_1$$

where the length $L_1$ of the nonwoven fabric having high-stretch regions and low-stretch regions (in the machine direction, in a natural state without tensile force) has undergone heat shrinkage to length $L_2$ (machine direction, natural state) after the heating step, i.e. in the stretchable nonwoven fabric.

In an embodiment as shown in FIG. 1, where the heated fluid passes through the interior of the nonwoven fabric to be heated, the nonwoven fabric to be heated is preferably heated from the moving conveyor side. This is in order to minimize rising of the nonwoven fabric to be heated from the moving conveyor and resistance (friction) during heat shrinkage.

When heated fluid is blown so as to press the nonwoven fabric to be heated against the moving conveyor, this has caused problems in that the nonwoven fabric to be heated becomes pressed against the moving conveyor, inhibiting its heat shrinkage, and the fibers of the nonwoven fabric to be heated become entangled in the moving conveyor.

The stretchable nonwoven fabric produced by the method of the present disclosure, subjected to heat shrinkage in the machine direction after the heating step, in comparison to one that has not passed through a heating step, i.e. a nonwoven fabric having high-stretch regions and low-stretch regions, has high elongation whiteness of the extensible fibers, and in particular has low 100% strength which is important for an absorbent article, satisfactory feel on the skin, and easy spreading.

A stretchable nonwoven fabric formed by the method of the present disclosure is useful for absorbent articles such as sanitary products and disposable diapers, cleaning products such as wipers, and medical goods such as masks.

EXAMPLES

The present disclosure will now be described using examples and comparative examples, with the understanding that it is in no way limited to the examples.

The measuring conditions for the evaluated properties in the examples and comparative examples were as follows.
[Fiber Size]
The fiber size was determined as the arithmetic mean of fiber sizes of 50 arbitrarily picked-up fibers in a sample observed at 300× magnification with an acceleration voltage of 5 kV using a VE-7800 Real Surface View microscope by Keyence Corp.
[Basis Weight]
The basis weight was measured according to JIS L 1906, 5.2.
[Bulk]
The bulk was measured using a THICKNESS GAUGE UF-60 by Daiei Kagaku Seiki Mfg. Co., Ltd.
[Strength and Elongation]
The strength and elongation were measured using a Model AG-KNI autograph tensile tester by Shimadzu Corp.

A sample with a 50 mm width was anchored to a chuck with a chuck distance of 100 mm, and extended at a pull rate of 100 mm/min. The maximum value of the strength obtained during extension was recorded as the "maximum point strength", and the elongation at that time was recorded as the "maximum point elongation". Also, the strength at 100% extension (twice the original length) is referred to as the "100% strength".

The denotation "MD" in the tables means the machine direction during formation.

Example 1

As a nonwoven fabric to be treated there was prepared a nonwoven fabric having a three-layer structure: extensible fiber layer/elastic fiber layer/extensible fiber layer.

The elastic fiber layer was a spunbond nonwoven fabric (basis weight: 5 g/m$^2$) composed of polypropylene-based elastomer fibers (melting point: approximately 161° C., density: approximately 0.87 g/cm$^3$, fiber size: approximately 20 μm).

The extensible fiber layer was a spunbond nonwoven fabric (basis weight: 10 g/m$^2$) composed of polypropylene fibers (melting point: approximately 160° C., fiber size: approximately 20 μm).

Also, the three-layer nonwoven fabric had rhomboid thermocompression bonded sections with sides of approximately 0.6 mm, integrated with an arrangement in a zigzag fashion in the machine direction and the cross direction at a pitch of about 2.5 mm. The area ratio of the thermocompression bonded sections was about 11%.

The nonwoven fabric to be treated had a basis weight of 25.9 g/m$^2$, a bulk of 0.23 mm, a strength (MD) of 26.3 N and a ductility (MD) of 176%.

The nonwoven fabric to be treated was gear-stretched with a gear stretcher such as shown in FIG. 1, to form a nonwoven fabric having high-stretch regions and low-stretch regions. The gear stretching conditions were as follows.

Gear pitch: 2.2 mm

Gear tooth cutting depth: 3.6 mm

Draw ratio: 245%

Residual strain after non-homogeneous stretching: 40%

Next, using the heating apparatus 21 shown in FIG. 1, warm air at 90° C. was passed through the nonwoven fabric having high-stretch regions and low-stretch regions for 4.8 seconds at a wind speed of 0.9 m/sec, to produce stretchable nonwoven fabric No. 1. In FIG. 1, the transport speed of the roller corresponding to the transport roller 8 was set to about 30 m/min and the transport speed of the roller corresponding to the transport roller 8' was set to about 22 m/min, for free heat shrinkage of the nonwoven fabric having high-stretch regions and low-stretch regions.

The heat shrinkage factor of stretchable nonwoven fabric No. 1 was evaluated.

Examples 2 to 10 and Comparative Example 1

A heating step was carried out according to Example 1, except that the warm air temperature and heating time were changed to the conditions listed in Table 1, to produce stretchable nonwoven fabric Nos. 2 to 10. The stretchable nonwoven fabric No. 11 was not subjected to a heating step, i.e. it was a nonwoven fabric having high-stretch regions and low-stretch regions.

The heat shrinkage factors of stretchable nonwoven fabric Nos. 2 to 11 were measured. The results are summarized in Table 1. The relationship between the temperature, heating time and heat shrinkage factor is illustrated in FIG. 3.

TABLE 1

| No. | Temperature (° C.) | Heating time (sec) | Heat shrinkage factor (%) |
|---|---|---|---|
| Example 1 | 90 | 4.8 | 83 |
| Example 2 | 100 | 4.8 | 79 |
| Example 3 | 110 | 4.8 | 78 |
| Example 4 | 120 | 4.8 | 76 |
| Example 5 | 90 | 2.4 | 91 |
| Example 6 | 100 | 2.4 | 89 |
| Example 7 | 110 | 2.4 | 86 |
| Example 8 | 120 | 2.4 | 84 |
| Example 9 | 130 | 2.4 | 80 |
| Example 10 | 140 | 2.4 | 80 |
| Comp. Ex. 1 | — | — | 100 |

Figure 3:
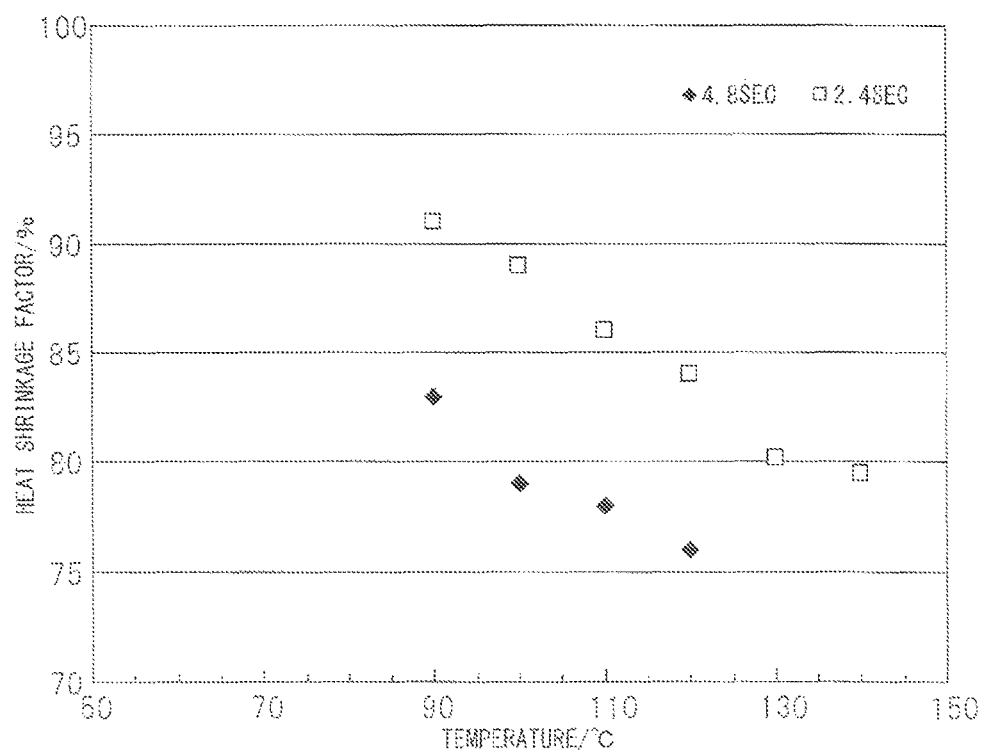
FIG. 3 is a graph showing the relationship between heat shrinkage factor and the conditions of temperature and time during the heating step.

Based on Table 1 and FIG. 3 it is seen that a higher heating step temperature and a longer time results in a smaller heat shrinkage factor, i.e. more heat shrinkage.

Next, the strengths and ductilities of stretchable nonwoven fabric Nos. 1 to 3 and 11 of Examples 1 to 3 and Comparative Example 1 were evaluated. Specifically, stretchable nonwoven fabric Nos. 1 to 3 and 11 were extended in the machine direction during production using a tensile tester. The results are shown in Table 2 and FIG. 4.

TABLE 2

| Stretchable nonwoven fabric No. | Heat shrinkage factor (%) | Basis weight (g/m$^2$) | Tensile test (MD) | | |
|---|---|---|---|---|---|
| | | | 100% strength (N) | Maximum point strength (N) | Maximum point elongation (%) |
| 1 | 83 | 24.1 | 2.83 | 33.4 | 154 |
| 2 | 79 | 26.2 | 2.33 | 36.1 | 178 |
| 3 | 78 | 26.2 | 2.52 | 37.4 | 178 |
| 11 | 100 | 20.0 | 8.62 | 22.9 | 128 |

Based on Table 2, stretchable nonwoven fabric Nos. 1 to 3 had lower 100% strengths than stretchable nonwoven fabric No. 11, suggesting satisfactory feel on the skin and easy spreading when used in absorbent articles such as disposable diapers. Also, stretchable nonwoven fabric Nos. 1 to 3 had higher maximum point strengths and maximum point elongations than stretchable nonwoven fabric No. 11, suggesting resistance to tearing when worn and long-term durability, when used in absorbent articles such as disposable diapers.

Specifically, the present disclosure relates to the following aspects J1 to J12.

[J1]

A method of producing a stretchable nonwoven fabric comprising the steps of:

non-homogeneous stretching of a nonwoven fabric to be treated comprising elastic fiber and extensible fiber while transporting the nonwoven fabric to be treated so that a nonwoven fabric having high-stretch regions and low-stretch regions is formed, and heating the nonwoven fabric having high-stretch regions and low-stretch regions for 0.1 to 10 seconds at a temperature of 40° C. or higher and below the melting point of the elastic fiber, wherein the nonwoven fabric having high-stretch regions and low-stretch regions has the high-stretch regions and low-stretch regions alternating in the machine direction, each parallel to the direction perpendicular to the machine direction.

[J2]

The method according to J1, wherein in the step of heating, heating is performed so that the nonwoven fabric having high-stretch regions and low-stretch regions undergoes heat shrinkage in a range of 30% to 99%.

[J3]

The method according to J1 or J2, wherein the step of heating is carried out by placing the nonwoven fabric having high-stretch regions and low-stretch regions on a support, and passing a heated fluid from the side of the support in the thickness direction of the nonwoven fabric having high-stretch regions and low-stretch regions.

[J4]

The method according to J3, wherein the heated fluid has a flow rate of 0.1 to 3.0 m/s.

[J5]

The method according to any one of J1 to J4, wherein the nonwoven fabric to be treated has a layered structure comprising an elastic fiber layer and an extensible fiber layer.

[J6]

The method according to any one of J1 to J5, wherein the nonwoven fabric to be treated has a three-layer structure comprising two extensible fiber layers and an elastic fiber layer therebetween.

[J7]

The method according to any one of J1 to J5, wherein the nonwoven fabric to be treated comprises a layer composed of elastic fiber and extensible fiber.

[J8]

The method according to any one of J1 to J5, wherein the elastic fiber and extensible fiber form composite fiber.

[J9]

The method according to any one of J1 to J8, wherein the step of non-homogeneous stretching is carried out by passing the nonwoven fabric to be treated through the gap between a pair of gear rolls with rotational axis lines that are perpendicular to the machine direction, and rotating while a plurality of teeth situated on the outer peripheral surfaces of the pair of gear rolls and arranged parallel to the rotational axis lines are mutually engaged.

[J10]

The method according to any one of J1 to J9, wherein the elastic fiber is fiber composed of a thermoplastic elastomer.

[J11]

The method according to any one of J1 to J10, wherein the elastic fiber is fiber composed of a polyolefin-based elastomer.

[J12]

The method according to any one of J1 to J11, wherein the transport speed of the elastic fiber after the step of heating is slower than the transport speed of the nonwoven fabric having high-stretch regions and low-stretch regions before the step of heating.

[J13]

A stretchable nonwoven fabric produced by the method according to any one of J1 to J12.

The invention claimed is:

1. A method of producing a stretchable nonwoven fabric, comprising:

non-homogeneous stretching of a nonwoven fabric to be treated including elastic fibers and extensible fibers, while transporting the nonwoven fabric to be treated in a machine direction so that high-stretch regions and low-stretch regions are formed in the nonwoven fabric, and after completion of said non-homogeneous stretching, heating the nonwoven fabric having the high-stretch regions and the low-stretch regions for 0.1 to 10 seconds at a temperature of 40° C. or higher and below a melting point of the elastic fibers, wherein in the nonwoven fabric having the high-stretch regions and the low-stretch regions the high-stretch regions and the low-stretch regions alternate in the machine direction, and are parallel to a direction perpendicular to the machine direction, and in said heating, the nonwoven fabric having the high-stretch regions and the low-stretch regions undergoes heat shrinkage in a range of 30% to 99%.

2. The method according to claim 1, wherein said heating is carried out by placing the nonwoven fabric having the high-stretch regions and the low-stretch regions on a support, and passing a heated fluid from a side of the support to the nonwoven fabric having the high-stretch regions and the low-stretch regions in a thickness direction of the nonwoven fabric having the high-stretch regions and the low-stretch regions.

3. The method according to claim 2, wherein the heated fluid has a flow rate of 0.1 to 3.0 m/s.

4. The method according to claim 1, wherein the nonwoven fabric to be treated has a layered structure comprising an elastic fiber layer of the elastic fibers, and an extensible fiber layer of the extensible fibers.

5. The method according to claim 1, wherein the nonwoven fabric to be treated has a three-layer structure comprising two extensible fiber layers of the extensible fibers, and an elastic fiber layer of the elastic fibers between the two extensible fiber layers.

6. The method according to claim 1, wherein the nonwoven fabric to be treated comprises a layer composed of the elastic fibers and extensible fibers mixed together.

7. The method according to claim 1, wherein the elastic fibers and extensible fibers form composite fibers.

8. The method according to claim 1, wherein said non-homogeneous stretching is carried out by passing the nonwoven fabric to be treated through a gap between a pair of gear rolls with rotational axis lines perpendicular to the machine direction while the pair of gear rolls are rotating and a plurality of teeth situated on outer peripheral surfaces of the pair of gear rolls and arranged parallel to the rotational axis lines are mutually engaged.

9. The method according to claim 1, wherein the elastic fibers are composed of a thermoplastic elastomer.

10. The method according to claim 1, wherein the elastic fibers are composed of a polyolefin-based elastomer.

11. The method according to claim 1, wherein a transport speed of the nonwoven fabric after said heating is slower than a transport speed of the nonwoven fabric having the high-stretch regions and the low-stretch regions before said heating.

12. A stretchable nonwoven fabric produced by the method according to claim 1.

13. The method according to claim 1, wherein said heating causes the extensible fibers to be oriented in a thickness direction of the nonwoven fabric having the high-stretch regions and the low-stretch regions.

14. The method according to claim 1, wherein the extensible fibers have a fiber size in a range of 1 μm to about 30 μm.

15. The method according to claim 14, wherein the fiber size of the extensible fibers is smaller than that of the elastic fibers.

16. The method according to claim 1, wherein a stress applied to the nonwoven fabric to be treated at said non-homogeneous stretching is lower than an elastic limit of the elastic fibers of the nonwoven fabric to be treated.

17. The method according to claim 1, wherein in said heating, the nonwoven fabric having the high-stretch regions and the low-stretch regions undergoes heat shrinkage in the range of 30% to 99% in the machine direction.

18. The method according to claim 1, wherein an elastic limit of the extensible fibers is smaller than that of the elastic fibers.

* * * * *